United States Patent [19]

Samejima et al.

[11] Patent Number: 4,963,365
[45] Date of Patent: Oct. 16, 1990

[54] CONTROLLED RELEASE DOSAGE FORM

[75] Inventors: Masayoshi Samejima, Mino; Kazuo Noda, Takarazuka; Masao Kobayashi, Kyoto; Shigeyuki Ishikawa, Mino, all of Japan

[73] Assignee: Tanabe Seiyaku Co., Ltd., Osaka, Japan

[21] Appl. No.: 267,085

[22] Filed: Nov. 4, 1988

[30] Foreign Application Priority Data

Nov. 6, 1987 [JP] Japan .................................. 62-281189

[51] Int. Cl.$^5$ .............................................. A61K 9/62
[52] U.S. Cl. .................... 424/46 L; 424/462; 424/493; 424/494; 424/495; 424/497; 427/3
[58] Field of Search ............. 424/472, 473, 480, 46 L, 424/462, 493, 494, 495; 427/3

[56] References Cited

U.S. PATENT DOCUMENTS

| | | |
|---|---|---|
| 2,921,883 | 1/1960 | Reese et al. . |
| 2,928,770 | 3/1960 | Bardani . |
| 3,492,397 | 1/1970 | Peters et al. . |
| 4,390,406 | 1/1982 | Guley et al. ............................ 424/21 |
| 4,600,645 | 7/1986 | Ghebre-Sellassie et al. ........ 428/403 |
| 4,681,755 | 7/1987 | Colombo et al. .................... 424/486 |
| 4,780,318 | 10/1988 | Applgren et al. .................... 424/469 |
| 4,795,644 | 1/1989 | Zentner ................................ 424/482 |
| 4,842,867 | 6/1989 | Ayer et al. .......................... 424/473 |
| 4,851,228 | 7/1989 | Zentner et al. ..................... 424/456 |

FOREIGN PATENT DOCUMENTS

| | | |
|---|---|---|
| 0092060 | 10/1983 | European Pat. Off. . |
| 0148811 | 7/1985 | European Pat. Off. . |
| 149920 | 7/1985 | European Pat. Off. . |
| 163000 | 12/1985 | European Pat. Off. . |
| 0220670 | 6/1987 | European Pat. Off. . |
| 60-4120 | 1/1985 | Japan . |
| 857550 | 12/1960 | United Kingdom . |

Primary Examiner—Thurman K. Page
Attorney, Agent, or Firm—Browdy and Neimark

[57] ABSTRACT

A controlled release dosage form which consists essentially of a core containing a medicament; an inner coating layer composed of ethylcellulose and a hydrophobic substance; and an outer coating layer containing a medicament are disclosed. Said dosage form shows rapid increase in blood concentration of the medicament and at the same time maintains the high level of the blood concentration over a prolonged period time.

7 Claims, 4 Drawing Sheets

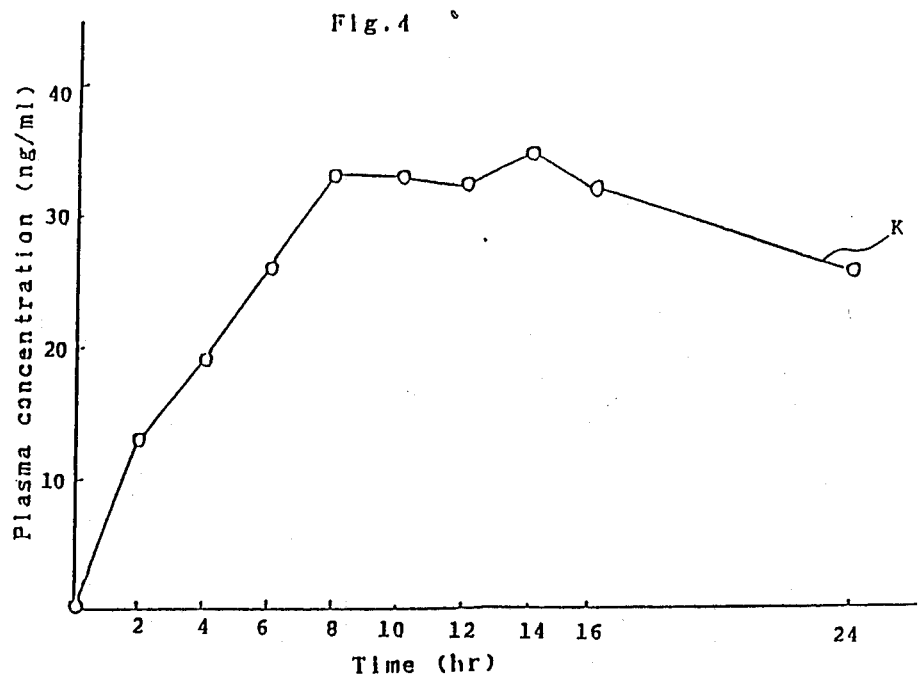

CONTROLLED RELEASE DOSAGE FORM

This invention relates to a controlled release pharmaceutical dosage form and a process for preparing same.

Various techniques for releasing drugs over an extended period of time have heretofore been known in the prior arts. For example, European Patent Publication No. 149920 discloses a controlled absorption pharmaceutical formulation comprising pellets having (i) a core of diltiazem in association with an organic acid and lubricant and (ii) an outer membrane which permits release of diltiazem in an aqueous medium. Further, a dosage form of pinacidil is prepared by the steps of coating a pinacidil-containing core with an enterosoluble polymer such as methacrylic acid-methylmethacrylate co-polymer, and then applying the layer containing pinacidil onto the surface of the core coated as above (Chemical Abstract, 102, 172661 g(1985), Japanese Patent Publication (unexamined), No. 4120/1985).

An object of the present invention is to provide a controlled release dosage form which is able to control the release of a medicament, i.e., to obtain a therapeutically effective blood level of the medicament rapidly after the oral administration thereof and at the same time maintain such effective blood level over an extended period of time. Another object of the invention is to provide a process for preparation of the controlled dosage form by simpler procedures as compared with known methods.

Namely, according to the present invention there is provided a controlled release pharmaceutical dosage form which consists essentially of a core containing a medicament, an inner coating layer composed of ethylcellulose and a hydrophobic substance, and an outer coating layer containing a medicament.

In making said controlled release dosage form, a pharmaceutically active compound or a mixture of a pharmaceutically active compound and excipients such as diluents, binders, lubricants or anti-aggregating agents can be used as the cores containing a medicament. The cores are preferably used in the form of granules or fine granules having a particle size of 300 $\mu$m–2000 $\mu$m, especially 500 $\mu$m–850 $\mu$m, in diameter. Although the hydrophobic cores have been used in some known methods for retarding the release of drugs from the dosage form, the cores of the invention are not necessarily hydrophobic and both of watersoluble and water-insoluble cores can be used in the present invention. Accordingly, a wide variety of excipients including diluents, binders, lubricants or anti-aggregating agents which are conventionally employed in this field can be used for preparing the cores of the present invention. Diluents which can be used in the present invention include, for example, saccharides such as sucrose, lactose or mannitol, starch, crystalline cellulose, calcium phosphate, calcium sulfate, calcium lactate and dextrose. Binders include, for example, polyvinyl alcohol, polyacrylic acid, polymethacrylic acid, polyvinylpyrrolidone, glucose, sucrose, lactose, maltose, sorbitol, mannitol, hydroxyethylcellulose, hydroxypropylmethylcellulose, hydroxypropylcellulose, macrogols, gum arabic, gelatin, agar and starch. Further, talc, magnesium stearate, calcium stearate, colloidal silica, stearic acid, waxes, hydrogenated oil, polyethylene glycols, sodium benzoate, sodium lauryl sulfate and magnesium lauryl sulfate are preferably used as lubricants or anti-aggregating agents.

The medicament-containing cores of the invention can be readily prepared according to conventional manners. For example, said medicament-containing cores may be prepared by mixing a medicament with an appropriate excipient or excipients (i.e., diluents, binders, lubricants, etc.), and then granulating the mixture by the wet extrusing granulation, tumbling granulation or fluidized bed granulation method as described in Remington's pharmaceutical Sciences 17th Edition, pages 1603 to 1632 (Mark Publishing Company, 1985). Alternatively, the medicament-containing cores may be prepared according to the tumbling granulation, pan-coating or fluidized bed coating method as described in Remington's pharmaceutical Sciences 17th Edition, pages 1633 to 1643. For example, a solution of a binder in a solvent (e.g., water, a lower alkanol such as methanol, ethanol, propanol, isopropanol or butanol, a lower alkanone such as acetone or methylethylketone, chloroform, dichloromethane, dichloroethane or a mixture thereof) is sprayed on the surface of inert carrier particles, and during said spraying, the mixture of a medicament and an excipient or excipients such as diluents or lubricants is added gradually thereto, thereby the medicament-containing core being readily obtained. In the latter case, any particles of 300 $\mu$m to 1500 $\mu$m in diameter which are made of sucrose, lactose, starch, crystalline cellulose or other inert materials may be used as the inert carrier particles.

Among the components of the inner coating layer to be formed on the surface of the medicament-containing cores, ethylcellulose should preferably be water insoluble ethylcellulose and have an ethoxy content of about 40–55%, especially about 43–51% and a viscosity of about 4–350 cP (measured in a 5 w/w% solution in toluene-ethanol (4:1) at 25° C.).

On the other hand, a wide variety of materials which are insoluble in water and easily mixed with ethylcellulose can be used as the hydrophobic substance. Example of the hydrophobic substance includes talc, alkali earth metal stearete such as magnesium stearate or calcium stearate, titanium oxide, precipitated calcium carbonate, zinc oxide, colloidal silica and the like. Among them, talc and alkali earth metal stearate are preferred, especially talc is most preferred for use in the invention. These hydrophobic substances are preferably in the form of fine particles having a diameter of 0.1 $\mu$m–100 $\mu$m, especially 0.1 $\mu$m–20 $\mu$m. In preparing the inner coating layer, the quantitative ratio of ethylcellulose to the hydrophobic substance is preferably in the range of about 1:1 to about 1:15 (by weight), especially about 1:2 to 1:4 (by weight).

The inner coating layer can be formed on the surface of the medicament-containing cores in a conventional coating method such as, for example, the fluidized bed coating or pancoating method as referred to above. The mixture of ethylcellulose and the hydrophobic substance to be sprayed on the medicamentcontaining cores may be used either in the form of a solution or a suspension. Water, a lower alkanol and a lower alkanone mentioned hereinbefore, chloroform dichloromethane, dichloroethane or a mixture thereof are suitable as a solvent for the coating solution or suspension. Said coating solution or suspension should preferably contain about 0.1–50%, especially 0.1–30% by weight, especially about 3–30%, more especialley 3–20% by weight, of the coating materials (i.e., ethylcellulose and the hydrophobic substance).

While the preferred coating ratio [(weight of ethylcellulose+hydrophobic substance/weight of the medicamentcontaining core) ×100] varies depending on the kind and content of medicaments, diluents, binders, lubricant or anti-aggregating agents to be incorporated in the core or desired release rate, said coating ratio is usually in the range of about 5-50%, especially about 5-40% and more especially about 10-30%.

In order to increase the accuracy for controlling the release rate of a medicament, a middle coating layer consisting of ethylcellulose alone or ethylcellulose and a water soluble substance may be, if desired, further coated on the surface of the inner coating layer prior to the coating of the outer coating layer. Suitable amount of ethylcellulose to be used as the middle coating layers is about 0.1-10%, especially about 1-5% by weight, of the amount of the core coated with the inner coating layer. Suitable examples of the water soluble substance which can be used for this purpose include sucrose, lactose, macrogols, mannitol and sorbitol. On the other hand, Ethylcellulose referred to above is preferably used for the middle coating layer. In case the water soluble substance is used together with ethylcellulose, preferred quantitative ratio of the water soluble substance to ethylcellulose is 1:1-20:1 (by weight). The coating of the middle coating layer can be carried out in the same manner as the coating of the inner coating layer, for example, by the fluidized bed coating or pancoating methods referred to above. Namely, said middle coating layer may be readily obtained by spraying on the surface of the inner coating layer a solution of ethylcellulose or a solution of ethylcellulose and the water soluble substance in a solvent (e.g., a lower alkanol, water or a mixture thereof). Alternatively, when a mixture of ethylcellulose and the water soluble substance is employed as the middle coating layer, said coating may also be carried out by spraying simultaneously a solution of ethylcellulose and a solution of the water soluble substance.

A medicament alone, or its admixture with an appropriate excipient or excipients such as diluents, binders, lubricants and/or anti-aggregating agents can be used as the outer coating layer. Any diluents, binders, lubricants or antiaggregating agents explained hereinbefore can be used. The amount of the medicament to be incorporated into the outer coating layer may be adjusted depending on the desired initial plasma level of the medicament. In general, however, suitable quantitative ratio of the medicament in the core to the medicament in the outer layer is in the range from about 1:1 to about 20:1 (by weight).

The outer coating layer can be prepared in a conventional manner, for example, by spraying a coating solution of the medicament or a coating solution containing the medicament and excipient(s) according to the fluidized bed coating or pancoating method referred to hereinbefore. Alternatively, said coating may be carried out by spraying the solution of the medicament (or the solution containing the medicament and a lubricant and/or an anti-aggrigating agent) and the solution of a binder simultaneously. Water, a lower alkanol, a lower alkanone, chloroform dichloromethane, dichloroethane or a mixture thereof are preferably used as a solvent. The particle size of the controlled release dosage form which is prepared as granules in the present invention should preferably be in the range of about 500 μm-2500 μm, especially 700 μm-2000 μm, in diameter.

The thus-obtained dosage form of the invention may be, if desired, further coated with, for example, sucrose, lactose, magnesium stearate, waxes, talc or a mixture thereof in a conventional manner.

When the controlled release dosage form of the invention having the multi-layered structure is administered orally to a warm blooded aminal such as human beings, the medicament incorporated in the outer coating layers is rapidly released therefrom. On the other hand, the release and dissolution rate of the medicament incorporated in the cores is controlled because the inner coating layer surrounding the core retards the penetration or diffusion of the digestive-juce into the cores and the release of the medicament through the layer. Especially, the dosage form of the invention is characterized in that the hydrophobic substance used to form the uniform inner coating layer is embedded in ethylcellulose matrix and improves the impermeability of ethylcellulose to give water-permeability on the inner coating layer. Moreover, said structure of the inner coating layer remains intact when the digestive-juice penetrates into the cores through the coating layers, and thus serves to release the medicament gradually at a constant rate. Accordingly, the dosage form of the invention, when administered, shows rapid increase in the blood concentration of the medicament and at the same time maintains the high level of the blood concentration of the medicament over a prolonged period of time because of the fast release of the medicament from the outer coating layer and also the controlled and sustained release of the medicament from the core.

The controlled release pharmaceutical dosage form of the present invention can be applied to a wide variety of drugs, medicaments or therapeutically active compounds. The drugs, medicaments or pharmaceutically active compounds to which the dosage form of the present invention can be applied include, for example, calcium-antagonist such as diltiazem hydrochloride, verapamil hydrochloride, nicardipine, nitrendipine or nimodipine; antasthmatics such as theophylline or trimethoquinol; watersoluble vitamins; antibiotics; antitumer agents; antipyretic, analgesic agents, blood sugar-lowering agents and so forth.

Further, the dosage form of the invention shows excellent bioavailability of the medicament and is quite effective to reduce the variation of blood level of the medicament, i.e., to minimize the variation between the highest and lowest blood concentrations thereof. Therefore, even when the minimum therapeutically effective blood level of a medicament is close to the toxic blood level thereof, the dosage form of the invention can be used to exert the therapeutic effect of such medicament while keeping the blood level thereof lower than the toxic level.

Besides, according to the present invention, a controlled release dosage form having uniformity in the content of the medicament can easily be prepared in simple manner by using a conventional apparatus. Furthermore, the dosage form of the invention is also advantageous in that the release rate of the medicament from the core can easily be controlled by changing the quantitative ratio of ethylcellulose to the hydrophobic substance to be used for the inner coating layers or changing the coating ratio of the inner coating layers.

EXAMPLE 1 (granules)

(1) The medicament-containing core

| (Ingredients) | (weight %) |
| --- | --- |
| Inert carrier particle | 17.5 |
| Diltiazem hydrochloride | 69.7 |
| Polyvinylpyrrolidone | 7.0 |
| Talc | 5.8 |
| Total | 100.0 |

800 g of the inert carrier particle (sucrose seeds of 20 to 24 meshes, Trade name: Non-pareil manufactured by Freund Industry Co.) are tumbled in the centrifugal fluidizing granulator (Freund Indusry Co., hereinafter, referred to as CF granulator). A mixture of 3200 g of diltiazem hydrochloride and 267 g of talc is spreaded onto the inert carrier particle gradually while spraying 3520 g of a polyvinylpyrrolidone-80% ethanol solution (polyvinylpyrrolidone content: 320 g) at a rate of 15 ml/min..

The products thus obtained are air-dried at 50° C. and then sieved, whereby about 4400 g of the medicament-containing core having the particle size of 10 to 20 meshes are obtained.

(2) Inner coating layer

| (Ingredients) | (weight %) |
| --- | --- |
| Medicament-containing core obtained in paragraph (1) | 87.0 |
| Ethylcellulose | 2.6 |
| Talc | 10.4 |
| Total | 100.0 |

4388 g of the medicament-containing core obtained in paragraph (1) are tumbled in the CF granulator. A solution of 133.2 g of ethylcellulose [ethoxy content: 48–49.5%, viscosity (measured at 25° C. with respect to a toluene-ethanol (4:1) solution: 9–11 cP] and 525.6 g of talc in 2530 g of 80% ethanol is sprayed onto the cores at a rate of about 30 ml/min. After the coating, the products are air-dried at 50° C. and then sieved, whereby about 5000 g of granules having the particle size of 10 to 20 meshes are obtained.

(3) Middle coating layer

| (Ingredients) | (weight %) |
| --- | --- |
| Granules obtained in paragraph (2) | 87.4 |
| Ethylcellulose | 1.5 |
| Sucrose | 11.1 |
| Total | 100.0 |

4907 g of granules obtained in paragraph (2) are tumbled in the CF granulator. A solution of 77 g of ethylcellulose [the ethoxy content and viscosity are the same as defined in paragraph (2) ] and 626.5 g of sucrose in 1463 g of 60% ethanol is sprayed onto the granules at a rate of about 30 ml/min. After the coating, the products are air-dried at 50° C. and then sieved, whereby about 5500 g of granules having the particle size of 10 to 20 meshes are obtained.

(4) Outer coating layer

| (Ingredients) | (weight %) |
| --- | --- |
| Granules obtained in paragraph (3) | 91.5 |
| Diltiazem hydrochloride | 8.5 |
| Total | 100.0 |

5450.2 g of granules obtained in paragraph (3) are tumbled in the CF granulator. A solution of 510 g of diltiazem hydrochloride in 2040 g of 60% ethanol is sprayed onto the granules at a rate of about 20 ml/min. After the coating, the products are air-dried at 50° C. and then sieved, whereby about 5850 g of granules having the particle size of 10 to 20 meshes are obtained.

(5) Surface coating layer

| (Ingredients) | (weight %) |
| --- | --- |
| Granules obtained in paragraph (4) | 92.3 |
| Sucrose | 7.1 |
| Talc | 0.6 |
| Total | 100.0 |

5837.5 g of granules obtained in paragraph (4) are tumbled in the CF granulator. A suspension of 450 g of sucrose and 40 g of talc in 460 g of 25% ethanol is sprayed onto the granules at a rate of about 25 ml/min. After the coating, the products are air-dried at 50° C. and then sieved, whereby about 6200 g of granules having the particle size of 10 to 20 meshes are obtained.

EXAMPLE 2 (granules)

(1) Middle coating layer

| (Ingredients) | (weight %) |
| --- | --- |
| Granules obtained in Example 1-(2) | 98.3 |
| Ethylcellulose | 1.7 |
| Total | 100.0 |

A solution of 84 g of ethylcellulose [the ethoxy content and viscosity are the same as defined in Example 1-(2)]in 1600 g of 80% ethanol is applied to 4907 g of granules obtained in Example 1—(2) in the same manner as described in Example 1—(3), whereby about 4900 g of granules having the particle size of 10 to 20 meshes are obtained.

(2) Outer coating layer

| (Ingredients) | (weight %) |
| --- | --- |
| Granules obtained in paragraph (1) | 89.8 |
| Ethylcellulose | 0.7 |
| Diltiazem hydrochloride | 9.5 |
| Total | 100.0 |

4891.2 g of granules obtained in paragraph (1) are tumbled in the CF granulator. A solution of 514.5 g of diltiazem hydrochloride and 41.2 g of ethylcellulose [the ethoxy content and viscosity are as defined in Example 1—(2)]in 3080 g of 70% ethanol is sprayed onto the granules at a rate of about 25 ml/min. After the coating, the products are air-dried at 50° C. and then sieved, whereby about 5300 g of granules having the particle size of 10 to 20 meshes are obtained.

(3) Surface coating layer

| (Ingredients) | (weight %) |
| --- | --- |
| Granules obtained in paragraph (2) | 83.6 |
| Sucrose | 13.8 |
| Talc | 2.6 |
| Total | 100.0 |

875.8 g of sucrose, 880 g of 25% ethanol and 163.2 g of talc are applied to 5288 g of granules obtained in paragraph (2) in the same manner as described in Example 1—(5), whereby about 6200 g of granules having the particle size of 10 to 20 meshes are obtained.

EXAMPLE 3 (granules)

Outer coating layer

| (Ingredients) | (weight %) |
|---|---|
| Granules obtained in Example 2-(1) | 87.7 |
| Diltiazem hydrochloride | 6.1 |
| Sucrose | 6.2 |
| Total | 100.0 |

4980 g of granules obtained in Example 2—(1) are tumbled in the CF granulator. 349 g of diltiazem hydrochloride is added gradually while a solution of 349g of sucrose in 25% ethanol is sprayed onto the granules at a rate of about 20 ml/min. After the coating, the products are air-dried at 50° C. and then sieved, whereby about 5450 g of granules having the particle size of 10 to 20 meshes are obtained.

EXAMPLE 4 (granules)

(1) Inner coating layer

| (Ingredients) | (weight %) |
|---|---|
| Medicament-containing core obtained in Example 1-(1) | 77.0 |
| Ethylcellulose | 11.5 |
| Talc | 11.5 |
| Total | 100.0 |

658.8 g of ethylcellulose [the ethoxy content and viscosity are the same as defined in Example 1—(2)], 658.8 g of talc and 6000 g of 80% ethanol are applied to 4388 g of the medicament-containing core obtained in Example 1-(1) in the same manner as described in Example 1-(2), whereby about 5600 g of granules having the particle size of 10 to 20 meshes are obtained.

(2) Outer coating layer

| (Ingredients) | (weight %) |
|---|---|
| Granules obtained in paragraph (1) | 94.1 |
| Ditiazem hydrochloride | 5.9 |
| Total | 100.0 |

5547 g of granules obtained in paragraph (1) are tumbled in the CF granulator. A solution of 350 g of diltiazem hydrochloride in 1400 g of 25% ethanol is sprayed onto the granules at a rate of about 30 ml/min. After the coating, the products are air-dried at 50° C. and then sieved, whereby about 5780 g of granules having the particle size of 10 to 20 meshes are obtained.

(3) Surface coating layer

| (Ingredients) | (weight %) |
|---|---|
| Granules obtained in paragraph (2) | 92.1 |
| Sucrose | 7.4 |
| Talc | 0.5 |
| Total | 100.0 |

459 g of sucrose, 34 g of talc and 60 g of 25% ethanol are applied to 5712 g of granules obtained in paragraph (2) in the same manner as described in Example 1-(5), whereby about 6000 g of granules having the particle size of 10 to 20 meshes are obtained.

EXAMPLES 5 to 7 (granules)

The inner coating layer, outer coating layer and surface coating layer are successively formed on 4388 g of the medicament-containing cores obtained in Example 1-(1) in the same manner as described in Example 4 except that the ingredients shown in following Table 1 are used for the inner coating layer. About 6000 g of granules having the particle size of 10 to 20 meshes are obtained, respectively.

TABLE 1

| | Ingredients of the inner coating layer (weight %) | | | |
|---|---|---|---|---|
| Example Nos. | Medicament-containing core obtained in Example 1-(1) | Ethyl-cellulose* | Talc | Total |
| 5 | 77.0 | 7.6 | 15.4 | 100.0 |
| 6 | 77.0 | 4.6 | 18.4 | 100.0 |
| 7 | 77.0 | 1.4 | 21.6 | 100.0 |

*The ethoxy content and viscosity are the same as defined in Example 1-(2)

EXAMPLES 8 to 11 (granules)

(1) Inner coating layer

The inner coating layer is applied to 4388 g of the medicament-containing cores obtained in Example 1-(1) in the same manner as described in Example 1-(2) except that the ingredients shown in following Table 2 are used for the inner coating layer. Granules having the particle size of 10 to 20 meshes are obtained.

TABLE 2

| | Ingredients of the inner coating layer (weight %) | | | |
|---|---|---|---|---|
| Example Nos. | Medicament-containing core obtained in Example 1-(1) | Ethyl-cellulose* | Talc | Total |
| 8-(1) | 90.9 | 1.5 | 7.6 | 100.0 |
| 9-(1) | 83.3 | 2.8 | 13.6 | 100.0 |
| 10-(1) | 76.9 | 3.9 | 19.2 | 100.0 |
| 11-(1) | 71.4 | 4.8 | 23.8 | 100.0 |

*The ethoxy content and viscosity are the same as defined in Example 1-(2)

(2) Outer coating layer

Granules obtained in paragraph (1) and diltiazem hydrochloride are treated in the same manner as described in Example 4-(2) except that the ingredients shown in table 3 are used for the outer coating layer. Granules having the particle size of 10 to 20 meshes are obtained. The yields of the granules are shown in Table 3.

TABLE 3

| Example Nos. | Ingredients (weight %) | | | Yields of the granules (Grams) |
|---|---|---|---|---|
| | Granules obtained in the paragraph (1) | Diltiazem hydrochloride | Total | |
| 8-(2) | 93.1 | 6.9 | 100.0 | ca. 4900 |
| 9-(2) | 93.6 | 6.4 | 100.0 | ca. 5200 |
| 10-(2) | 94.1 | 5.9 | 100.0 | ca. 5750 |
| 11-(2) | 94.5 | 5.5 | 100.0 | ca. 6200 |

EXAMPLES 12 to 13 (granules)

(1) Inner coating layer

The inner coating layer is applied to 4388 g of the medicament-containing cores obtained in Example 1-(1) in the same manner as described in Example 1-(2) except that magnesium stearate in an amount shown in the following Table 4 is used instead of talc.

TABLE 4

| Example Nos. | Ingredients of the inner coating layer (weight %) | | | |
|---|---|---|---|---|
| | Medicament-obtained in containing core Example 1-(1) | Ethyl-cellulose* | stearate | Total |
| 12-(1) | 90.9 | 1.9 | 7.2 | 100.0 |
| 13-(1) | 83.3 | 3.4 | 13.3 | 100.0 |

*:The ethoxy content and viscosity are the same as defined in Example 1-(2)

(2) Outer coating layer

Granules obtained in paragraph (1) and diltiazem hydrochloride are treated in the same manner as described in Example 4-(2). Granules having the particle size of 10 to 20 meshes are obtained. The amount of ingredient used and the yields of the granules are shown in Table 5.

TABLE 5

| Example Nos. | Ingredients (weight %) | | | Yields of the granules (Grams) |
|---|---|---|---|---|
| | Granules obtained in the paragraph(1) | Diltiazem hydrochloride | Total | |
| 12-(2) | 93.6 | 6.4 | 100.0 | ca. 5200 |
| 13-(2) | 94.1 | 5.9 | 100.0 | ca. 5700 |

EXAMPLE 14 (capsules)

Granules obtained in Example 1 are filled in hard capsules No. 3 to give the capsules containing 100 mg of diltiazem hydrochloride in each capsule.

EXAMPLE 15 (capsules)

Granules obtained in Example 2 are filled in hard capsules No. 3 to give the capsules containing 100 mg of diltiazem hydrochloride in each capsule.

EXAMPLE 16 (GRANULES)

(1) Medicament-containing core

| (Ingredients) | (weight %) |
|---|---|
| Inert carrier particle | 8.0 |
| Theophylline | 56.0 |
| Sucrose | 16.0 |
| Total | 100.0 |

1400 g of the inert carrier particle (sucrose seeds of 20 to 40 meshes, Trade name: Non-pareil, manufactured by Freund Industry Co.) are tumbled in the CF granulator. 2800 g of theophylline are spreaded thereto gradually while spraying 3200 ml of a 25% aqueous sucrose solution onto the seeds at a rate of 15 ml/min. The products thus obtained are air-dried at 50° C. and then sieved, whereby about 4400 g of granules having the particle size of 10 to 20 meshes are obtained.

(2) Inner coating layer

| (Ingredients) | (weight %) |
|---|---|
| Medicament-containing core obtained in pararaph (1) | 84.4 |
| Ethylcellulose | 2.6 |
| Talc | 13.0 |
| Total | 100.0 |

4220 g of the medicament-containing core obtained in paragraph (1) are tumbled in the CF granulator. A solution of 130.0 g of ethylcellulose [the ethoxy content and viscosity are the same as defined in Example 1-(2)] and 650.0 g of talc in 2530 g of 80% ethanol is sprayed onto the granules at a rate of about 30 ml/min. After the coating, the products are air-dried at 50° C. and then sieved, whereby about 4950 g of granules having the particle size of 10 to 20 meshes are obtained.

(3) Outer coating layer

| (Ingredients) | (weight %) |
|---|---|
| Granules obtained in pargraph (2) | 74.0 |
| Theophylline | 17.5 |
| Sucrose | 8.5 |
| Total | 100.0 |

4800 g of the granules obtained in paragraph (2) are tumbled in the CF granulator. 1135 g of theophylline are spreaded thereto gradually while spraying 920 ml of a 60% aqueous sucrose solution onto the granules at a rate of about 20 ml/min. The products thus obtained are air-dried at 50° C. and then sieved, whereby about 6400 g of granules having the particle size of 10 to 20 meshes are obtained.

EXAMPLE 17 (GRANULES)

(1) Inner coating layer

| (Ingredients) | (weight %) |
|---|---|
| Medicament-containing core obtained in Example 16-(1) | 84.4 |
| Ethylcellulose | 1.7 |
| Talc | 13.9 |
| Total | 100.0 |

4220 g of the medicament-containing core obtained in Example 16-(1), 85.0 g of ethylcellulose, 695.0 g of talc and 600 g of 80% ethanol are treated in the same manner as described in Example 16-(2), whereby about 4900 g of granules having the particle size of 10 to 20 meshes are obtained.

(2) Outer coating layer

| (Ingredients) | (weight %) |
|---|---|
| Granules obtained in paragraph (1) | 74.0 |
| Theophylline | 17.5 |
| Sucrose | 8.5 |
| Total | 100.0 |

4800 g of granules obtained in paragraph (1) and 1135 g of theophylline are treated in the same manner as described in Example 16-(3), whereby about 6400 g of granules having the particle size of 10 to 20 meshes are obtained.

EXAMPLES 18 TO 22 (GRANULES)

The inner coating layer, outer coating layer and surface coating layer are successively formed on the medicamentcontaining cores obtained in Example 1-(1) in the same manner as described in Example 1-(2) - (5) except that a hydriphybic substance shown in Table 6 is used for the inner coating layer instead of talc.

Granules having the particle size of 10 to 20 meshes are obtained.

TABLE 6

| Example Nos. | The hydrophobic substance used for the inner coating layer |
| --- | --- |
| 18 | calcium stearate |
| 19 | titanium oxide |
| 20 | precipitated calcium carbonate |
| 21 | zinc oxide |
| 22 | colloidal silica |

EXAMPLES 23 TO 26 (GRANULES)

The inner coating layer, outer coating layer and surface coating layer are successinely formed on the medicament-containing cores obtained in Example 1-(1) in the same manner as described in Example 1-(2) - (5) except that a water soluble material shown in Table 7 is used for the middle coating layer inslead of sucrose. Granules having the prcticle size of 10 to 20 meshes are obtained.

TABLE 7

| Example Nos. | Water soluble substance used for the middle layer |
| --- | --- |
| 23 | lactose |
| 24 | macrogol 6000 |
| 25 | mannitol |
| 26 | sorbitol |

EXPERIMENT 1 (DISSOLUTION TEST)

The effect of the quantitative ratio of ethylcellulose and a hydrophobic substance in the inner coating layer on the dissolution rate of the medicament is investigated by using the granules of Examples 4 to 7.

[SAMPLE USED]

1: Granules obtained in Example 4-(3)
2: Granules obtained in Example 5
3: Granules obtained in Example 6
4: Granules obtained in Example 7

[TEST METHOD]

Dissolution test was performed according to the second dissolution test method (Paddle Method) specified in THE PHARMACOPOEIA OF JAPAN 10th-edition by adding each sample of the granules (dose of diltiazem hydrochloride : 100 mg) to 900 ml of distilled water under stirring at 100 rpm at 37° C. 10 ml of the solution was collected at intervals and the dissolution percentage of the medicament (diltiazem hydrochloride) was calculated based on the absorbance of the sample solution measured at 285 nm.

[RESULTS]

The results are shown in FIG. 1. The curves A, B, C and D in FIG. 1 show time-course changes in the dissolution percentages of the medicament (diltiazem hydrochloride) from the granules of Examples 4, 5, 6 and 7, respectively. From these results, it is demonstrated that various dissolution patterns of the medicament are available by adjusting the quantitative ratio of ethylcellulose and talc in a range of 1:1 to 1:15.

EXPERIMENT 2 (DISSOLUTION TEST)

The effect of the coating amount of the inner coating layer on the dissolution rate of the medicament is investigated according to the test method described in Experiment 1 by using the granules of Examples 8 to 11.

[SAMPLES]

1: Granules obtained in Example 8
2: Granules obtained in Example 9
3: Granules obtained in Example 10
4: Granules obtained in Example 11

[RESULTS]

The results are shown in FIG. 2. The curves E, F, G and H in FIG. 2 show time-course changes in the dissolution percentage of the medicament from the granules of Examples 8, 9, 10 and 11, respectively. From these results, it is shown that the dissolution patterns of the medicament can be also controlled by adjusting the coating amounts of the inner coating layer.

EXPERIMENT 3 (DISSOLUTION TEST)

The dissolution percentages of the medicament from the dosage form of the present invention are investigated according to the test method described in Experiment 1 by using the capsules obtained in Examples 14 and 15.

[RESULTS]

The results are shown in FIG. 3. The curves I and J in FIG. 3 show the time-course changes in the dissolution percentage of the medicament from the capsules of Examples 14 and 15, respectively. From these results, it is clear that the dissolution rate of the dosage form of the present invention is well controlled over a prolonged period of time.

EXPERIMENT 4 (DISSOLUTION TEST)

The dissolution tests of the granules obtained in Example 12, 13, 16 and 17 are performed in accordance with the test method described in Experiment 1. In this experiment, the dissolution rate of theophylline is determined based on the absorbance of the sample solution measured at 292 nm.

[RESULTS]

The dissolution percentages of the medicament (theophylline) are shown in Table 8.

TABLE 8

| Samples | Percentage of dissolution (%) Time (hr) | | | | | | | |
| --- | --- | --- | --- | --- | --- | --- | --- | --- |
|  | 0.5 | 1 | 3 | 5 | 7 | 10 | 14 | 20 |
| Granules in Exp. 12 | 11 | 12 | 18 | 26 | 40 | 65 | 89 | 100 |
| Granules in Exp. 13 | 10 | 11 | 14 | 18 | 20 | 26 | 39 | 66 |
| Granules in Exp. 16 | 35 | 37 | 43 | 49 | 55 | 68 | 80 | 92 |
| Granules in Exp. 17 | 40 | 46 | 67 | 85 | 95 | 100 | 100 | 100 |

EXPERIMENT 5 (MEASUREMENT OF PRASMA LEVEL)

One capsule obtained in Example 15 (dose of the diltiazem hydrochloride: 100 mg) is orally administered together with 100 ml of water to healthy volunteers (adult male, body weight: 55 to 68 kg). Blood samples are collected at intervals from the vein of forearms, and then plasma samples were obtained therefrom by centrifugation. The concentrations of the medicament (diltiazem hydrochloride) in plasma are determined by using high performance liquid chromatography.

[RESULTS]

The results are shown in FIG. 4. In this figure, the curve shows the plasma levels of the medicament (diltiazem hydrochloride). From these results it is demonstrated that the dosage form of the present invention shows a prolonged plasma profile of the medicament with a suitable initial plasma level thereof.

[BRIEF DESCRIPTION OF DRAWING]

FIG. 4 shows graphs of plasma levels versus time after oral administration of capsule of Example 15.

Figure 1:
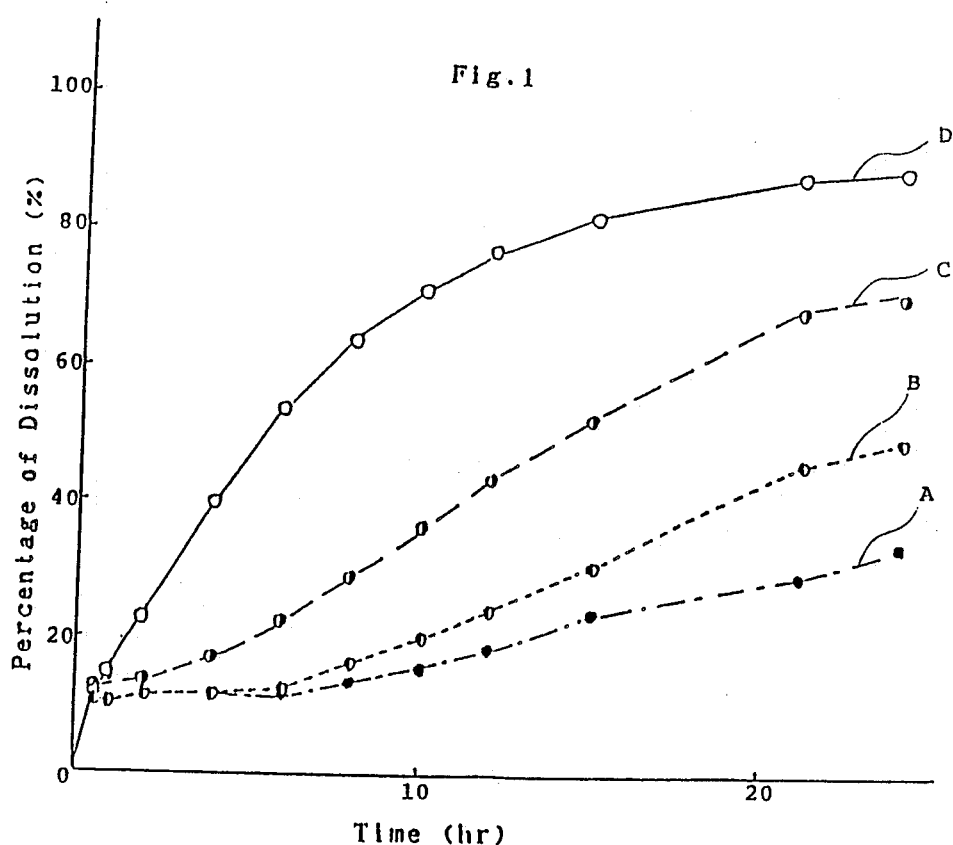
FIGS. 1, 2 and 3 show graphs of dissolution percentage versus time of granules (or capsules) of Examples 4 to 7, Examples 8 to 11, and Examples 14 to 15, respectively.
Figure 2:
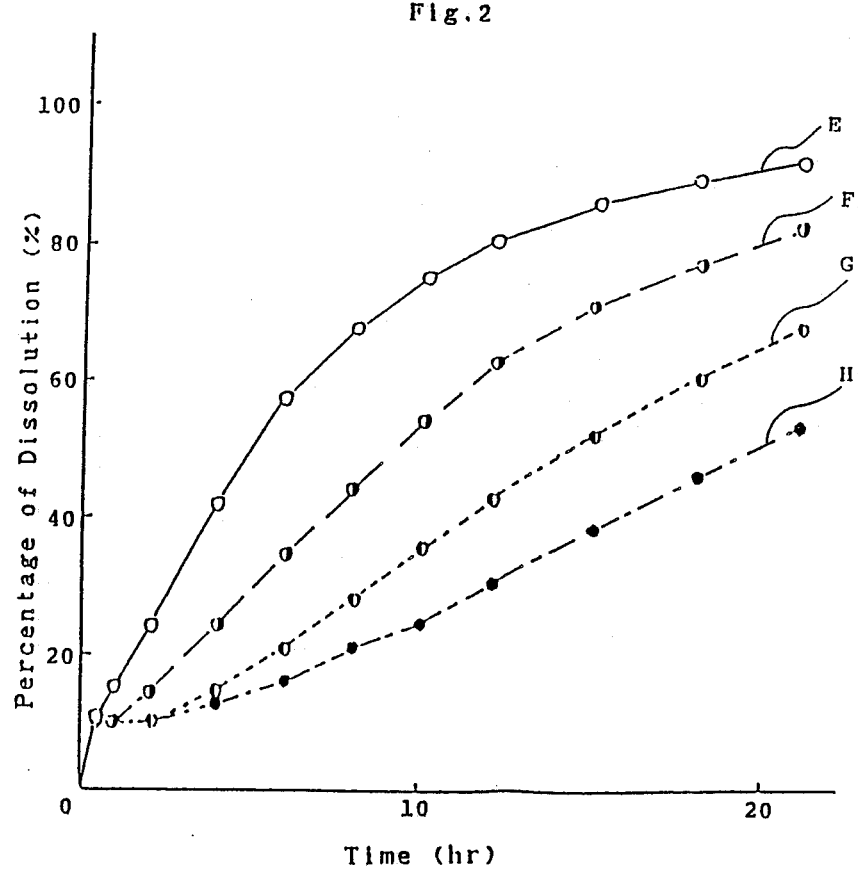
Figure 3:
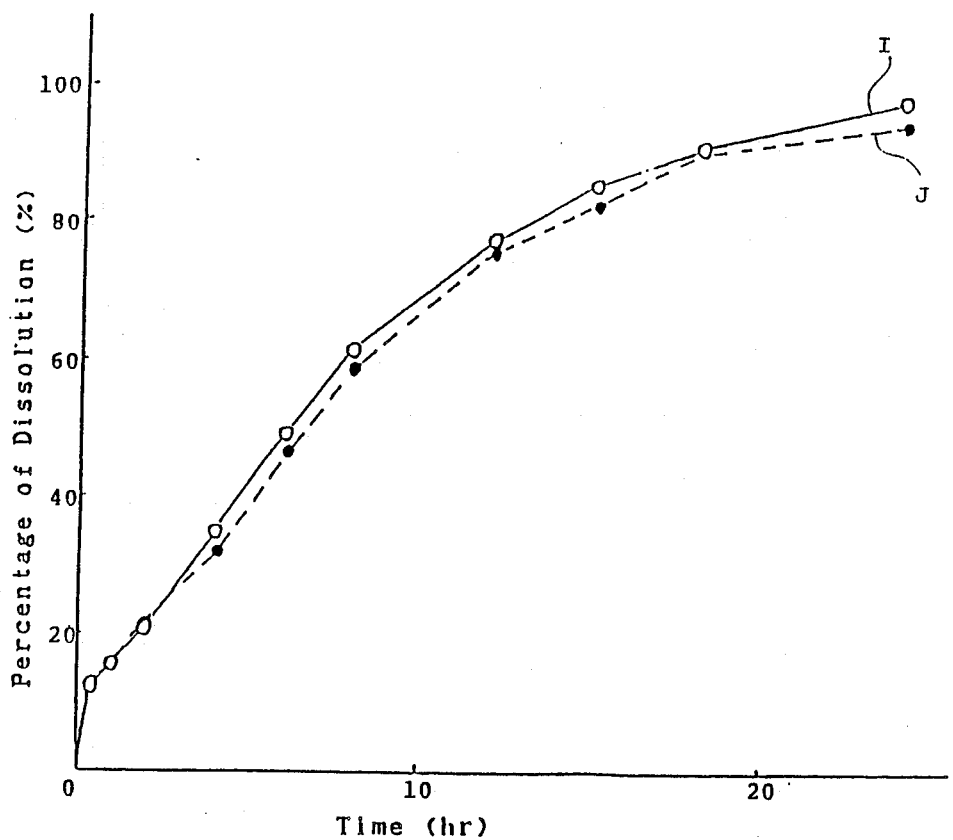

What we claim is:

1. A controlled release pharmaceutical dosage from which consists essentially of a water-soluble core containing diltiazem hydrochloride; an inner coating layer composed of ethylcellulose and a hydrophobic substance selected from the group consisting of talc and an alkali earth metal stearate, the quantitative ratio of ethylcellulose to said hydrophobic substance being in the range of about 1:1 to about 1:15 by weight; and an outer coating layer containing diltiazem hydrochloride.

2. The controlled release dosage form claimed in claim 1 in which a middle coating layer composed of ethylcellulose alone or a mixture of ethylcellulose and a water-soluble substance selected from the group consisting of sucrose, lactose, macrogol, mannitol and sorbitol, the quantitative ratio of said water soluble substance to said ethylcellulose being in the range of about 1:1 to about 20:1 by weight, is further formed between the inner coating layer and the outer coating layer.

3. The controlled release dosage form claimed in claim 2, in which the quantitative ratio of the medicament incorporated in the core to the medicament incorporated in the outer coating layer is within a range of 1:1 to 20:1 (by weight).

4. The controlled dosage form claimed in claim 3, in which the particle size of the medicament-containing core is in the range of 300 $\mu$m to 2000 $\mu$m in diameter, the coating ratio [(weight of ethylcellulose + hydrophobic substance/weight of the medicament-containing core) $\times$ 100] of the inner coating layer is in the range of 5–50%, and the amount of ethylcellulose to be used in the middle coating layer is in the range of 0.1 to 10% of the amount of the inner coating layer-coated core.

5. The controlled release dosage form claimed in claim 3, in which said dosage form is granules having a particle size of 500 $\mu$m to 2500 $\mu$m in diameter.

6. The controlled release dosage form claimed in claim 4, in which the hydrophobic substance is talc, magnesium stearate or calcium strearate.

7. The controlled release dosage form claimed in claim 6, in which the hydrophobic substance is talc.

* * * * *